United States Patent [19]

Vartanian et al.

[11] 4,098,585
[45] Jul. 4, 1978

[54] AMINE-ALKENYLSUCCINIC ACID OR ANHYDRIDE REACTION PRODUCT

[75] Inventors: Paul F. Vartanian; Joseph B. Biasotti, both of Wappingers Falls, N.Y.

[73] Assignee: Texaco Inc., New York, N.Y.

[21] Appl. No.: 693,459

[22] Filed: Jun. 7, 1976

[51] Int. Cl.$^2$ .................. C10L 1/18; C07D 207/24
[52] U.S. Cl. .................. 44/63; 252/51.5 A; 260/326.5 F; 260/326.5 FM
[58] Field of Search ............. 44/63, 71; 252/51.5 A; 260/326.5 F, 326.5 FM

[56] References Cited

U.S. PATENT DOCUMENTS

| 2,944,025 | 7/1960 | Verdol | 44/71 X |
|---|---|---|---|
| 3,151,957 | 10/1964 | Clough et al. | 44/71 X |
| 3,223,495 | 12/1965 | Calvino et al. | 44/71 X |
| 3,452,002 | 6/1969 | Bresch | 44/63 X |
| 3,497,334 | 2/1970 | Gee et al. | 44/71 |
| 3,773,479 | 11/1973 | Dorn et al. | 44/71 |
| 3,846,093 | 11/1974 | Feldman | 44/63 X |
| 3,920,698 | 11/1975 | Haemmerle et al. | 260/326.5 FM |
| 4,048,080 | 9/1977 | Lee et al. | 252/51.5 A |
| 4,049,564 | 9/1977 | Ryer et al. | 252/51.5 A |
| 4,049,565 | 9/1977 | Nnadi et al. | 252/51.5 A |

*Primary Examiner*—Daniel E. Wyman
*Assistant Examiner*—Thomas A. Waltz
*Attorney, Agent, or Firm*—Thomas H. Whaley; Carl G. Ries; James J. O'Loughlin

[57] ABSTRACT

An amine-alkenylsuccinic acid or anhydride reaction product in which the alkenyl radical has a moleculer weight ranging from about 250 to 3000, and a motor fuel composition containing said amine-alkenylsuccinic acid or anhydride are provided.

31 Claims, No Drawings

AMINE-ALKENYLSUCCINIC ACID OR ANHYDRIDE REACTION PRODUCT

BACKGROUND OF THE INVENTION

1. Field of the Invention

Carburetor detergents for motor fuel compositions produced by the reaction of an alkenylsuccinic acid or anhydride with an amine or polyamine are well known. These products are obtained by reacting an alkenylsuccinic acid or anhydride with the amine or polyamine under thermal conditions to produce an alkenyl succinimide or an alkenylsuccinamic acid depending on the temperature of the reaction which effects water removal. No amine or polyamine substituent is added to the alkenyl radical in the alkenylsuccinic acid or anhydride in this reaction.

Alkenylsuccinic acids or anhydrides have also been chlorinated followed by a reaction with an amine or a polyamine under thermal reaction conditions to produce an effective detergent. This reaction produces a reaction product in which a portion of the amine or polyamine reactant is directly attached to the alkenyl radical of the alkenylsuccinic acid or anhydride. A nitrogen to carbon linkage between the amine and the alkenyl radical takes place following the splitting off of hydrogen chloride in this process.

2. Description of the Prior Art

The prior art to which this invention relates includes the following patents, U. S. Pat. Nos: 3,676,089, 3,443,918, 3,905,781, 3,497,334, 3,256,074, 3,223,495, 3,148,960, 2,982,633 and British Pat. No. 1,383,423. The last mentioned discloses a reaction between hydrocarbons and polyamines employing a free-radical initiator to produce a motor fuel detergent. This application is related to Ser. No,. 693,458 filed on June 7, 1976 which disclosure is incorporated in the present application.

SUMMARY OF THE INVENTION

A principal object of the present invention is to provide a novel detergent reaction product. Another object is to provide a detergent reaction product which exhibits a relatively high nitrogen content.

A further object is to provide a detergent reaction product which exhibits a novel structure as a result of the reaction of an amine with an alkenylsuccinic acid or anhydride.

Still another object is to provide a method for preparing a novel detergent additive.

A further object is to provide a novel motor fuel composition containing the amine-alkenylsuccinic acid or anhydride reaction product of the invention.

It has now been found that an amine including substituted amines and polyamines and their derivatives noted below, can be reacted with an alkenylsuccinic acid or anhydride in the presence of a free radical initiator. This reaction leads to the production of a unique reaction product designated herein as an amine-alkenylsuccinic acid or as an amine-alkenylsuccinic anhydride reaction product. When this reaction has been conducted employing certain amine or polyamine reactants, the reaction product has been found to possess a higher level of nitrogen than obtained in known processes using the same reactants. It is postulated that this higher nitrogen content is due to the production of a structurally unique reaction product involving the addition of a portion of the amine directly on to the alkenyl radical of the alkenylsuccinic acid or anhydride in addition to that added via imide formation. Moreover, this new structure is theorized to be characterized by a new carbon to carbon bond linkage between the amine reactant and the alkenyl radical at the site of its olefinic bond.

The amine-alkenylsuccinic acid or anhydride reaction product of the invention is effective as a detergent and as a corrosion inhibitor in a motor fuel composition. It is important that this novel reaction product is essentially ashless, i.e., it does not form ash deposits in the intake manifold, the carburetor, or the combustion zone of the engine. This feature allows the formulation of improved motor fuel compositions which exhibit improved engine performance.

DESCRIPTION OF THE PREFERRED EMBODIMENTS

The novel amine-alkenylsuccinic acid or anhydride reaction product is obtained by reacting an alkenylsuccinic acid or anhydride, having the structural unit represented by the formula:

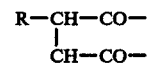

in which R is an alkenyl radical having an average molecular weight ranging from about 250 to 3000 with an amine, represented by the formula:

in which R' and R" represent hydrogen or a monovalent alkyl, aminoalkyl or hydroxyalkyl radical having from 1 to 8 carbon atoms, X is a divalent hydrocarbon radical having from 2 to 8 carbon atoms and Y is a radical, selected from the group consisting of hydrogen, amino, hydroxy and a radical having the formula O(R'''O)$_x$H in which R''' is an alkylene radical having from 2 to 3 carbon atoms and $x$ is an integer from 1 to 5, in the presence of a free-radical initiator using a molar proportion of said amine to said alkenylsuccinic acid or anhydride greater than 1.

The alkenyl radical on the alkenylsuccinic acid or anhydride reactant has an average molecular weight ranging from about 250 to 3000 as determined by the ASTM D-2503 Method. A particularly effective alkenylsuccinic acid or anhydride starting reactant is one in which the alkenyl radical has an average molecular weight ranging from about 500 to 2000. Alkenylsuccinic acid or anhydride reactants in which the alkenyl radical has a molecular weight ranging from about 750 to 1500 are preferred additives as fuel detergents.

The alkenyl radical on the alkenylsuccinic acid or anhydride reactant is obtained in the polymerization of a monoolefin according to known methods. Thus, monoolefins having from 2 to 6 carbon atoms, such as ethylene, propylene, 1-butene, 2-butene, isobutylene, amylene, hexylene and mixtures thereof are polymerized to produce monoolefinic polymers or copolymers having an appropriate average molecular weight according to known methods. The monoolefinic polymer or copolymer is then reacted with maleic anhydride to produce the alkenylsuccinic acid or anhydride reactant employed in the production of the reaction product of this invention. The procedures referred to are well known in the art and the processes involved do not constitute any part of the present invention.

The amine reactant employed to product the reaction product of the invention is represented by the formula:

in which R' and R" represent hydrogen or a monovalent alkyl, aminoalkyl or hydroxyalkyl radical having from 1 to 8 carbon atoms, X is a divalent hydrocarbon radical having from 2 to 8 carbon atoms, and Y is a radical, selected from the group consisting of hydrogen, amino, hydroxy and a radical having the formula O(R''' O)$_x$H in which R''' is an alkylene radical having from 2 to 3 carbon atoms and $x$ is an integer from 1 to 5.

Monoamines which can be employed to produce the reaction product of the invention include ethylamine, propylamine, butylamine, dimethylamine and diethylamine. The preferred monoamines are the alkyl and dialkyl monoamines having from 1 to about 6 carbon atoms.

Polyamines which can be employed as the amine reactant include the alkylene polyamines, such as ethylenediamine, propylene diamine, butylene diamine, diethylene triamine, triethylene tetramine, tetraethylene pentamine, pentaethylene hexamine, dipropylene triamine, trimethylene diamine, tetramethylene diamine, pentamethylene diamine, hexamethylene diamine and the like.

Additional nitrogen-containing reactants which are effective include the hydroxy-substituted amines such as ethanolamine, propanolamine, butanolamine, diethanolamine and the N-(aminoalkyl)substituted morpholines and piperazines in which the alkyl radical has from 1 to 3 carbon atoms.

Alkoxylated amines, obtained by alkoxylating an amine with from about 1 to 5 moles of an alkylene oxide, such as ethylene oxide and propylene oxide, are also suitable reactants for the reaction product of the invention.

In preparing the reaction product of the invention, the molar proportion of the amine reactant to the alkenylsuccinic acid or anhydride reactant employed is greater than 1. A preferred molar proportion of the amine to the alkenylsuccinic acid or anhydride are proportions in the range from about 1.5 to 10 moles of amine per mole of alkenylsuccinic acid or anhydride. It is particularly preferred to employ a molar proportion ranging from about 2 to 5 moles of amine per mole of the alkenylsuccinic acid or anhydride.

The present process for the production of a novel amine-alkenylsuccinic acid or anhydride reaction product is conducted in the presence of conventional initiators which decompose to form free radicals. Suitable initiators include the organic peroxides, for example the dialkyl peroxides, the azo, and the diazo compounds. Highly effective initiators include azobisisobutyronitrile, benzoyl peroxide, di-t-butyl peroxide, isopropyl peroxy carbonate, t-butyl peroxy isopropyl carbonate and t-butyl perbenzoate.

The free radical initiator is employed in a proportion ranging from about 0.1 to 2.0 weight percent of the initiator based on said alkenylsuccinic acid or anhydride. The preferred concentration of the free-radical initiator is from about 0.75 to about 1.25 weight percent.

The alkenylsuccinic acid or anhydride reactant employed in the preparation of the reaction product of this invention can have a variety of structural formulas. The structure of the alkenyl radical will vary depending on the source of the olefin polymer from which it is formed. An alkenylsuccinic acid formed from a polypropylene of 750 average molecular weight is represented by a formula as follows:

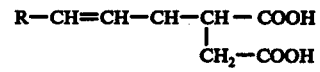

where R is the balance of the polypropylene radical.

An alkenylsuccinic anhydride formed from a polyisobutylene of 1100 average molecular weight is represented by the formula:

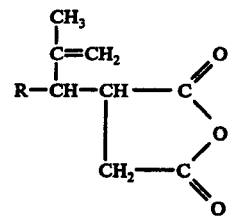

in which R is the balance of the polyisobutylene polymer.

It will be appreciated that an olefin polymer, such as polyisobutylene, can have the olefin bond in a number of positions. The different polymeric structures are known as the vinylidene type, the terminal vinyl type and the trisubstituted type, the latter of which is the predominant type. Reacting the trisubstituted type polyisobutylene with maleic anhydride produces the polyisobutenylsuccinic anhydride illustrated above.

The reaction of an alkenylsuccinic acid or anhydride with an amine will result in the production of an alkenylsuccinamic acid or an alkenylsuccinimide according to known procedures depending on the temperature of the reaction. In these reactions, no amine reacts with the alkenyl radical portion of the noted reactant.

According to the present invention, novel products are produced wherein the amine reactant, or a portion thereof, reacts at the olefinic bond in the alkenyl radical of the alkenylsuccinic acid or anhydride. This reaction is believed to occur substantially simultaneously with a reaction involving the acid or anhydride moiety of the alkenylsuccinic acid or anhydride.

In the reaction of an amine having the formula: H$_2$N — X — Y, in which X and Y have the values noted above with the propenylsuccinic anhydride in accordance with this invention, it is postulated that the reaction product will contain a novel compound corresponding to the formula:

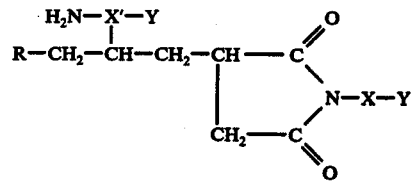

In the reaction of an amine, having the formula: H$_2$N — X — Y in which X and Y have the values noted above with a polyisobutenylsuccinic anhydride according to this invention, it is postulated that the reaction product will contain a novel compound corresponding to the formula:

$$CH_3 - \underset{\underset{CH_3}{|}}{\overset{\overset{CH_3}{|}}{C}} - \left[ CH_2 - \underset{\underset{CH_3}{|}}{\overset{\overset{CH_3}{|}}{C}} \right]_y - \underset{\underset{\underset{\underset{O}{||}}{C}}{\underset{|}{CH_2}}}{CH} - \underset{N-X-Y}{\overset{\overset{CH_3}{|}\;\;\;\overset{NH_2}{|}}{CH - CH_2 - X' - Y}} - C=O$$

in which y is a number from about 4 to 50 and preferably from about 12 to 26.

It will be appreciated that X' has a value similar to X with the exception that a hydrogen atom has been removed or transferred to the alkenyl radical as a result of the reaction. A mixture of amines can be employed in the reaction leading to the noted compounds so that the hydrogen atoms on the amine attached to the alkenyl radical are represented by R' and R'' having the values disclosed above while x has a value which can be determined from the average molecular weight of the alkenyl radical employed in the starting reactant.

The following examples illustrate preparation of the novel detergent additive of the invention.

EXAMPLE I 100 grams (0.053 mole based on active anhydride) of polyisobutenylsuccinic anhydride in which the polyisobutenyl radical has an average molecular weight of 1290, 15 grams (0.25 mole) of ethylenediamine and 0.75 gram of azobisisobutyronitrile are charged to a reactor and heated with stirring to 90° C. These reaction conditions are maintained for three hours. The reaction product is cooled to room temperature, dissolved in 100 milliliters of hexane and twice washed with 100 milliliters of 90% aqueous methanol. The hexane solvent is evaporated off by heating under a nitrogen stream to yield the reaction product. This reaction product has the following analysis: % $N$ = 1.7.

EXAMPLE II 100 grams (0.072 mole) polyisobutenylsuccinic anhydride in which the polyisobutenyl radical has an average molecular weight of 750, 15 grams (0.25 mole) of ethylenediamine and 1 gram of azobisisobutyronitrile are charged to a reactor and reacted as in Example I above.

98 grams of a reaction product are recovered having the following analysis: % $N$ = 2.17.

EXAMPLE III 100 grams (0.053 mole) polyisobutenylsuccinic anhydride in which the polyisobutenyl radical has an average molecular weight of 1290, 15 grams (0.147 mole) of N,N-dimethylpropane-1,3-diamine and 1 gram of azobisisobutyronitrile are charged to a reactor and reacted as in Example I above.

108 grams of a reaction product are recovered having the following analysis: % $N$ = 1.6.

EXAMPLE IV 100 grams (0.053 mole) polyisobutenylsuccinic anhydride in which the polyisobutenyl radical has an average molecular weight of 1290, 25 grams (0.098 mole) ethoxylated-ethylenediamine in which the average of four ethylene oxide radicals have reacted with each ethylene diamine, and 1 gram of azobisisobutyronitrile are charged to a reactor and reacted as in Example I above.

115 grams of a reaction product are recovered having the following analysis: % $N$ = 2.2.

EXAMPLE V 100 grams (0.053 mole) of polyisobutenylsuccinic anhydride in which the polyisobutenyl radical has an average molecular weight of 1290, 20 grams (0.194) of diethylenetriamine, and 1 gram of azobisisobutyronitrile are charged to a reactor and reacted as in Example I above.

102 grams of a reaction product were recovered having the following analysis: % $N$ = 2.4.

EXAMPLE VI 110 grams (0.059 mole) of polyisobutenylsuccinic anhydride in which the polyisobutenyl radical has an average molecular weight of 1290, 16.5 grams (0.275 mole) of ethylenediamine, and 1.1 grams of t-butylperoxy isopropyl carbonate are charged to a reactor and reacted as in Example I. The reaction product had the following analysys: % $N$ = 1.5.

EXAMPLE VII 100 grams (0.162 mole) of polyisobutenylsuccinic anhydride in which the polyisobutenyl radical has an average molecular weight of 335, 50 grams (0.347 mole) N-(3-aminopropyl)morpholine, and 2 grams of azobisisobutyronitrile are charged to a reactor and reacted as in Example 1 above. The reaction product is cooled to room temperature, dissolved in 100 ml of hexane and once washed with 100 ml of 90% aqueous methanol. The hexane is removed as in Example I.

96 grams of a reaction product are recovered with the following analysis % $N$ = 7.36.

EXAMPLE VIII 100 grams (0.162 mole) of polyisobutenylsuccinic anhydride in which the polyisobutenyl radical has an average molecular weight of 335, 40 grams (0.667 mole) of ethylenediamine, and 2 grams of azobisisobutyronitrile are charged to a reactor and reacted as in Example I above.

78 grams of a reaction product are recovered with the following analysis: % $N$ = 3.3

EXAMPLE IX 100 grams (0.021 mole) of polyisobutenylsuccinic anhydride in which the polyisobutenyl radical has an average molecular weight of 2300, 10 grams (0.167 mole) of ethylenediamine, and 1 grams of azobisisobutyronitrile are charged to a reactor and heated with stirring at 90°. The reaction conditions are maintained for three hours. The reaction product is cooled to room temperature, dissolved in 100 ml of hexane and twice washed with 100 ml of 90% aqueous methanol. The hexane solvent is evaporated off by heating under a nitrogen stream to yield the reaction product.

EXAMPLE X 100 grams (0.053 mole) of polyisobutenylsuccinic anhydride in which the polyisobutenyl radical has an average molecular weight of 1290, 15 grams (0.246 mole) of ethanolamine, and 1 gram of azobisisobutyronitrile are charged to a reactor and reacted as in Example I above.

EXAMPLE XI 100 grams (0.053 mole) of polyisobutenylsuccinic anhydride in which the polyisobutenyl radical has an average molecular weight of 1290, 15 grams (0.238 mole) of butylamine, and 1 gram of azobisisobutyronitrile are charged to a reactor and reacted as in Example I.

EXAMPLE XII 100 grams (0.053 mole) of polyisobutenylsuccinic anhydride in which the polyisobutenyl radical has an average molecular weight of 1290, 15 grams (0.25 mole) of ethylenediamine, and 1 gram of benzoyl peroxide are charged to a reactor and reacted as in Example I except that the temperature is maintained at 100° C.

EXAMPLE XIII 100 grams (0.053 mole) of polyisobutenylsuccinic anhydride in which the polyisobutenyl radical has an average molecular weight of 1290, 15 grams (0.250 mole) of ethylenediamine, and 1 gram of t-butylperbenzoate are charged to a reactor and reacted as in Example I except that the temperature is maintained at 110° F for 10 hours.

EXAMPLE XIV 100 grams (0.079 mole) of polypropenyl succinic anhydride in which the polypropenyl radical has an average molecular weight of 850, 15 grams (0.250 mole) of ethylenediamine, and 1 gram of azobisisobutyronitrile are charged to a reactor and reacted as in Example I above.

EXAMPLE XV 100 grams (0.053 mole) of polyisobutenylsuccinic anhydride in which the polyisobutenyl radical has an average molecular weight of 1290, 20 grams (0.230 mole) of N-(2-aminoethyl)morpholine, and 1 gram of azobisisobutyronitrile are charged to a reactor and reacted as in Example I above.

EXAMPLE XVI 100 grams (0.053 mole) of polyisobutenylsuccinic anhydride in which the polyisobutenyl radical has an average molecular weight of 1290. 50 grams (0.265 mole) of tetraethylenepentamine, and 1 gram of azobisisobutyronitrile are charged to a reactor and reacted as in Example I above.

EXAMPLE XVII 100 grams (0.053 mole) of polyisobutenylsuccinic anhydride in which the polyisobutenyl radical has an average molecular weight of 1290, 30 grams (0.233 mole) of n-octylamine, and 1 gram of azobisisobutyronitrile are charged to a reactor and reacted as in Example I above.

EXAMPLE XVIII 100 grams (0.072 mole) of polyisobutenylsuccinic anhydride in which the polyisobutenyl radical has an average molecular weight of 750, 60 grams (0.205 mole) of propoxylated ethylenediamine in which four propylene oxide groups have been reacted with each ethylenediamine, and 1 gram of azobisisobutyronitrile are charged to a reactor and reacted as in Example I above.

EXAMPLE XIX 100 grams (0.053 mole) of polyisobutenylsuccinic anhydride in which the polyisobutenyl radical has an average molecular weight of 1290, 50 g (ca. 0.12 mole) of a polyethoxylated ethylenediamine in which more than four ethylene oxide radicals have reacted with the ethylenediamine, and 1 gram of azobisisobutyronitrile are charged to a reactor and reacted as in Example I above.

EXAMPLE XX 100 grams (0.053 mole) of polyisobutenylsuccinic anhydride in which the polyisobutenyl radical has an average molecular weight of 1290, 30 g. (0.233 mole) of dibutylamine, and 1 gram of azobisisobutyronitrile are charged to a reactor and reacted as in Example I above.

EXAMPLE XXI 100 grams (0.053 mole) of polyisobutenylsuccinic anhydride in which the polyisobutenyl radical has an average molecular weight of 1290, 40 grams (ca. 0.12 mole) of ethoxylated diethylenetriamine in which about five ethylene oxide radicals have reacted with each diethylene triamine, and 1 gram azobisisobutyronitrile are charged to a reactor and reacted as in Example I above.

EXAMPLE XXII 100 grams (0.053 mole) of polyisobutenylsuccinic anhydride in which the polyisobutenyl radical has an average molecular weight of 1290, 15 grams (0.15 mole) 2,2'-diaminodiethyl ether, and 1 gram of azobisisobutyronitrile are charged to a reactor and reacted as in Example I above.

The following are comparison examples in contrast to the reaction product of the invention.

EXAMPLE XXIII 58 grams (0.031 mole) of polyisobutenylsuccinic anhydride in which the polyisobutenyl radical has an average molecular weight of 1290, and 8.7 grams (0.145 mole) of ethylenediamine are charged to a reactor and reacted at a temperature of about 90° for three hours.

The crude reaction product is dissolved in hexane, washed with aqueous methanol and recovered by distilling the hexane. The reaction product has the following analysis: % $N$ = 1.56.

EXAMPLE XXIV 100 grams (0.072 mole) of polyisobutenylsuccinic anhydride in which the polyisobutenyl radical has an average molecular weight of 750, and 15 grams (0.25 mole) of ethylenediamine are charged to a reactor and reacted at a temperature of about 90° C for 3 hours.

The crude reaction product is dissolved in hexane, washed with aqueous methanol and recovered by distilling off the hexane. The reaction product has the following analysis: % $N$ = 1.86.

EXAMPLE XXV 100 grams (0.078 mole) polyisobutene of an average molecular weight of 1290, 30 grams (0.294 mole) N,N-dimethylpropane-1,3 diamine and 5.5 grams di-t-butylperoxide are charged to a reactor and reacted as in Example I above. 88 grams of a reaction product are recovered having the following analysis: % $N$ = 0.54%.

The novel detergent additive of the invention is effective in a gasoline or motor fuel composition. The base fuel for a motor fuel composition consists of a mixture of hydrocarbons boiling in the gasoline boiling range generally from about 90° to 450° F. This base fuel may consist of straight-chain or branched-chain paraffins, cycloparaffins, olefins, and aromatic hydrocarbons and any mixture of these. The base fuel can be derived from straight-run naphtha, polymer gasoline, natural gasoline or from catalytically cracked or thermally cracked hydrocarbons and catalytically reformed stocks. The hydrocarbon composition and the octane level of the base fuel are not critical. Any conventional motor fuel base may be employed in the practice of this invention.

In general, the additive of the invention is added to the fuel composition in a minor amount, i.e., an amount effective to provide detergency to the gasoline. The additive is effective in a motor fuel composition in amounts ranging from about 0.001 to 0.25 weight percent based on the total fuel composition. It is preferred to employ concentrations ranging from about 0.03 to 0.10 weight percent.

A fuel composition according to the invention will generally contain any of the additives normally employed in a motor fuel. For example, the base fuel may be blended with an anti-knock compound, such as tetraalkyl lead compound, including tetraethyl lead, tetramethyl lead, tetrabutyl lead, and chemical and physical mixtures thereof or cyclopentadienyl manganese tricarbonyl type compounds generally in a concentration from about 0.05 to 4.0 cc. per gallon of gasoline. The motor fuel composition may also be fortified with any of the known conventional additives including anti-icing additives, corrosion inhibitors and the like.

The additive of the invention was tested for its effectiveness as a carburetor detergent in the Carburetor Detergency Test. This test is run on a Chevrolet V-8 engine mounted on a test stand using a modified four barrel carburetor. The two secondary barrels of the carburetor are sealed and the feed to each of the primary barrels arranged so that an additive fuel can be run in one barrel and the base fuel run in the other. The primary carburetor barrels were also modified so that they had removable aluminum inserts in the throttle plate area in order that deposits formed on the inserts of this area could be conveniently weighed.

In the procedure designed to determine the effectiveness of an additive fuel to remove preformed deposits in the carburetor, the engine is run for a period of time, usually 24 to 48 hours, using the base fuel as the feed to both barrels with engine blow-by circulated to an inlet in the carburetor body. The weight of the deposits on both sleeves is determined and recorded. The engine is then cycled for 24 additional hours with a suitable reference fuel containing an effective detergent being fed to one barrel, the additive fuel of the invention to the other barrel and blowby to the inlet in the carburetor body. The inserts are then removed from the carburetor and weighed to determine the difference between the performance of the additive and reference fuels in removing the preformed deposits.

After the aluminum inserts are cleaned, they are replaced in the carburetor and the entire process repeated with the fuels reversed in the carburetor to minimize differences in fuel distribution and barrel construction. The deposit weights in the two runs are averaged and the effectiveness of the fuel composition of the invention is expressed in percent.

The Base Fuel employed with the detergent additive of the invention in the following examples was a premium grade gasoline having a Research Octane Number of about 99.9 and containing 3.1 cc. of tetraethyl lead per gallon. This gasoline consisted of about 23.5% aromatic hydrocarbons, 7.5% olefinic hydrocarbons and 69 paraffinic hydrocarbons and boiled in the range from 90° F to 360° F.

The carburetor detergency test results obtained with the fuel composition of the invention, a related detergent fuel composition, and Base Fuel are set forth in the table below.

TABLE I

| | CARBURETOR DETERGENCY TEST | |
|---|---|---|
| Run | Additive Fuel Composition | % Effective |
| 1 | Base Fuel + 50 PTB of Example I | +40 |
| 2 | Base Fuel + 50 PTB of Example II | +62 |
| 3 | Base Fuel + 50 PTB of Example III | +68 |
| 4 | Base Fuel + 50 PTB of Example XXV | 0 |
| 5 | Base Fuel (control) | −10 |

PTB = Pounds of additive per 1000 barrels of fuel

Runs 1, 2, and 3 which are illustrations of a motor fuel composition containing the reaction product of the present invention, i.e., of Examples I, II and III, exhibited a surprising improvement in carburetor detergency over base fuel.

The Colonial Pipe Line Rust Test is conducted by putting 300 cc. of the fuel sample into a 400 cc. beaker and immersing therein a steel spindle, 3 3/16 inches long and ½ inch wide made from ASTM D-655-60 polished steel. The test fuel and the steel spindle are maintained at 100° F for ½ hour. 30 cc. of distilled water are then added and its content are maintained at 100° F for 3½ hours. The spindle is removed and visually inspected and the percentage of rusted surface area is estimated. The base fuel used in this test was the motor fuel composition described above.

TABLE II

| | COLONIAL PIPELINE RUST TEST | |
|---|---|---|
| Run. | Fuel Composition | % Rust |
| 1. | Base Fuel (No Rust inhibitor) | 50-100 |
| 2. | Base Fuel + 12.5PTB Example I | Trace |
| 3. | Base Fuel + 5 PTB Example II | Trace-1 |
| 4. | Base Fuel + 5 PTB Example IV | Trace |

The foregoing tests show that the additive of the invention is outstandingly effective as a rust inhibitor for a light hydrocarbon fuel composition.

We claim:

1. A motor fuel composition comprising a mixture of hydrocarbons in the gasoline boiling range and a minor detergent amount of a reaction product prepared by the process which comprises reacting an alkenylsuccinic acid or anhydride compound, having the structural unit represented by the formula:

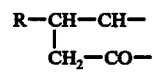

in which R is an alkenyl radical having a molecular weight ranging from about 250 to 3000, with an amine, represented by the formula:

in which R' and R" represent hydrogen or a monovalent alkyl, aminoalkyl or hydroxyalkyl radical having from 1 to 8 carbon atoms, X is a divalent hydrocarbon radical having from 2 to 8 carbon atoms and Y is a radical, selected from the group consisting of hydrogen, amino, hydroxy and a radical having the formula O(R'''O)$_x$H in which R''' is an alkylene radical having from 2 to 3 carbon atoms and x is an integer from 1 to 5, in the presence of a free radical initiator, selected from the group consisting of organic peroxides, azo and diazo compounds, the molar proportion of said amine to said succinic acid or anhydride being greater than one.

2. A motor fuel composition according to claim 1 in which said alkenyl radical in said alkenyl succinic compound has a molecular weight ranging from about 500 to 2000.

3. A motor fuel composition according to claim 1 in which said alkenyl radical in said alkenyl succinic compound has a molecular weight from about 750 to 1500.

4. A motor fuel composition according to claim 1 in which the molar proportion of said amine to said alkenyl-succinic acid or anhydride ranges from about 1.5 to 10.

5. A motor fuel composition according to claim 1 in which the molar proportion of said amine to said alkenyl succinic acid or anhydride ranges from 2 to 5.

6. A motor fuel composition according to claim 1 in which said alkenyl succinic compound is polyisobutenyl succinic anhydride and said polyisobutenyl radical has an average molecular weight ranging from 1050 to 1400.

7. A motor fuel composition according to claim 1 in which said alkenyl succinic compound is polypropylene succinic anhydride and said polypropylene radical has an average molecular weight ranging from 1050 to 1400.

8. A motor fuel composition according to claim 1 in which said amine is diethylenetriamine.

9. A motor fuel composition according to claim 1 in which said amine is tetraethylenepentamine.

10. A motor fuel composition according to claim 1 in which said amine is ethanolamine.

11. A motor fuel composition according to claim 1 in which said amine is alkoxylated with from 1 to 5 moles of an alkylene oxide per mole of amine.

12. A motor fuel composition according to claim 1 containing from about 0.001 to 0.25 weight percent of said reaction product.

13. A motor fuel composition for a four-cycle internal combustion gasoline engine according to claim 1 containing from about 0.003 to 0.10 weight percent of said reaction product.

14. A motor fuel composition comprising a mixture of hydrocarbons in the gasoline boiling range and a minor detergent amount of a reaction product prepared by the process which comprises reacting an alkenylsuccinic acid or anhydride compound, having the structural unit represented by the formula:

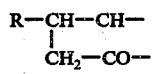

in which R is an alkenyl radical having a molecular weight ranging from about 250 to 3000 with ethylenediamine in the presence of a free radical initiator, the molar proportion of said ethylenediamine to said succinic acid or anhydride being greater than one.

15. A motor fuel composition according to claim 14 in which said alkenyl radical in said alkenyl succinic compound has a molecular weight from about 750 to 1500.

16. A reaction product prepared by the process which comprises reacting an alkenylsuccinic acid or anhydride compound having the structural unit represented by the formula:

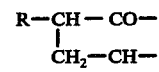

in which R is an alkenyl radical having a molecular weight ranging from about 250 to 3000 with an amine, represented by the formula:

in which R' and R" represent hydrogen or a monovalent alkyl, aminoalkyl or hydroxyalkyl radical having from 1 to 8 carbon atoms, X is a divalent hydrocarbon radical having from 2 to 8 carbon atoms and Y is a radical, selected from the group consisting of hydrogen, amino, hydroxy and a radical having the formula O(R'''O)$_x$H in which R''' is an alkylene radical having from 2 to 3 carbon atoms and x is an integer from 1 to 5, in the presence of a free radical initiator, selected from the group consisting of organic peroxides, azo and diazo compounds, the molar proportion of said amine to said succinic acid or anhydride being greater than one.

17. A reaction product according to claim 16 in which said alkenyl radical in said alkenyl succinic compound has a molecular weight ranging from about 500 to 2000.

18. A reaction product according to claim 16 in which said alkenyl radical in said alkenyl succinic compound has a molecular weight from about 750 to 1500.

19. A reaction product according to claim 16 in which said alkenylsuccinic compound is a polyisobutenylsuccinic anhydride.

20. A reaction product according to claim 16 in which said alkenylsuccinic compound is a polypropenylsuccinic anhydride.

21. A reaction product according to claim 16 in which the molar proportion of said amine to said alkenyl succinic acid or anhydride ranges from about 1.5 to 10.

22. A reaction product according to claim 16 in which the molar proportion of said amine to said alkenyl succinic acid or anhydride ranges from 2 to 5.

23. A reaction product according to claim 16 in which said alkenyl succinic compound is polyisobutenyl succinic anhydride and said polyisobutenyl radical has an average molecular weight ranging from 1050 to 1400.

24. A reaction product according to claim 16 in which said amine is diethylenetriamine.

25. A reaction product according to claim 16 in which said amine is tetraethylenepentamine.

26. A reaction product according to claim 16 in which said amine is ethanolamine.

27. A reaction product according to claim 16 in which said amine is alkoxylated with from 1 to 5 moles of an alkylene oxide per mole of amine.

28. A reaction product according to claim 27, in which said alkylene oxide is ethylene oxide.

29. A reaction product prepared by the process which comprises reacting an alkenylsuccinic acid or anhydride compound having the structural unit represented by the formula:

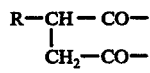

in which R is an alkenyl radical having a molecular weight ranging from about 250 to 3000 with ethylenediamine in the presence of a free radical initiator, the molar proportion of said ethylenediamine to said succinic acid or anhydride being greater than one.

30. A reaction product according to claim 29 in which said alkenyl radical in said alkenyl succinic compound has a molecular weight from about 750 to 1500.

31. A reaction product according to claim 29 in which said free radical initiator is azobisiso-butyronitrile.

* * * * *